United States Patent [19]

Worschech et al.

[11] Patent Number: 4,744,927

[45] Date of Patent: May 17, 1988

[54] SYNTHESIS OF DIBASIC ORGANO-LEAD COMPOUNDS IN MELT PHASE

[75] Inventors: Kurt Worschech; Peter Wedl, both of Loxstedt; Erwin Fleischer, Bremerhaven-Spaden; Frido Loeffelholz, Bremerhaven-Surheide, all of Fed. Rep. of Germany

[73] Assignee: Henkel Kommanditgesellschaft auf Aktien, Duesseldorf, Fed. Rep. of Germany

[21] Appl. No.: 805,487

[22] Filed: Dec. 5, 1985

[30] Foreign Application Priority Data

Dec. 5, 1984 [DE] Fed. Rep. of Germany ....... 3444259

[51] Int. Cl.$^4$ ................................................ C11C 1/00
[52] U.S. Cl. ...................................... 260/414; 556/82; 556/105
[58] Field of Search ................... 556/82, 105; 260/414

[56] References Cited

U.S. PATENT DOCUMENTS

| 1,729,823 | 10/1929 | Dimonig | 260/414 X |
|---|---|---|---|
| 1,830,984 | 11/1931 | Diggs et al. | 260/414 X |
| 3,002,943 | 10/1961 | Kebrich | 556/105 X |
| 3,072,693 | 1/1963 | Szczepanek et al. | 260/435 |
| 3,461,081 | 8/1969 | Sugahara et al. | 524/567 X |
| 3,519,571 | 7/1970 | Szczepanek et al. | 260/414 X |
| 3,546,263 | 12/1970 | Ruf | 556/105 X |
| 3,562,180 | 2/1971 | White et al. | 556/105 X |
| 3,639,264 | 2/1972 | Roussos et al. | 556/105 X |
| 3,803,188 | 4/1974 | Scott et al. | 260/414 X |
| 4,316,852 | 2/1982 | Blachford | 556/105 X |
| 4,324,768 | 4/1982 | Sugahara et al. | 556/105 X |
| 4,421,886 | 12/1983 | Worschech et al. | 524/310 |

FOREIGN PATENT DOCUMENTS

| 684155 | 12/1952 | United Kingdom . |
|---|---|---|
| 936533 | 9/1963 | United Kingdom . |
| 1173814 | 4/1968 | United Kingdom . |
| 1136935 | 12/1968 | United Kingdom . |

OTHER PUBLICATIONS

Search Report, European Patent Office, Application No. 85115046.6, Apr. 16, 1986.

Primary Examiner—Paul F. Shaver
Attorney, Agent, or Firm—Ernest G. Szoke; Henry E. Millson, Jr.; Mark A. Greenfield

[57] ABSTRACT

Dibasic lead-fatty acid salts and mixtures thereof with neutral lead-fatty acid salts are synthesized in a melt reaction using a free-hydroxyl organic compound as a catalyst/initiator. The resulting products are useful as stabilizers for halogen-containing polymers.

23 Claims, No Drawings

SYNTHESIS OF DIBASIC ORGANO-LEAD COMPOUNDS IN MELT PHASE

BACKGROUND OF THE INVENTION

1. Field of the Invention

The melt-reaction synthesis of dibasic plumbousfatty acid salts and their use as stabilizers in the production of rigid halogen-containing polymers.

2. Statement of the Related Art

Stabilizers based on lead compounds are widely used in the production of moldings of halogen-containing polymers, particularly rigid polyvinyl chloride. Stabilizer systems of this type are not only highly effective, they are also inexpensive. In addition, they provide the plastic end products with effective light stabilization. For many years, formulations containing stabilizers based on lead compounds have normally contained primary stabilizers, (also known as pigment stabilizers) because of their covering power. These stabilizers are generally basic lead sulfates.

Other suitable stabilizers are organic lead salts, particularly lead fatty acid soaps. Of particular importance are the commercial lead stearates which are used either as dibasic lead stearate, $2\, PbO.Pb(\text{fatty acid residue})_2$- 51% by weight lead stearate, or as neutral lead stearate $Pb(\text{fatty acid residue})_2$-28% by weight lead stearate. In many cases, combinations of these two are also used.

The stabilizer system is generally completed by calcium soaps, particularly commercial calcium stearate. These metal soaps may also be counted as part of the lubricant system which normally contains paraffins, optionally free fatty acids, other hydrocarbon waxes such as polyethylene derivatives, and, in some cases, fatty acid esters.

In recent years, the economic need to find less expensive formulations has resulted in the growing elimination of pigment stabilizers of the basic lead sulfate type. In addition, developments in the field of processing machines for plastics have meant that molding compositions based on halogen-containing polymers containing far less stabilizer can now be extruded without difficulty. Accordingly, the basic lead soaps $2PbO.Pb(\text{fatty acid residue})_2$ primarily stearates, are increasingly becoming the focus of interest as primary stabilizers. Neutral lead soaps (stearates) optionally together with calcium soaps (stearates) are being used as rheologically active constituents of the formulation and as co-stabilizers. By contrast, there has been little change in the other components of the stabilizers/lubricant systems still used for halogen-containing polymers.

Mixtures of the type in question here offer the incentive to produce the entire stabilization and rheology system in the form of a melt compound. Proposals to that effect can be found, for example, in U.S. Pat. No. 3,461,081 and U.K. Pat. No. 1,136,935, as well as their corresponding German Pat. Nos. 1,544,697 and 1,569,190. These publications describe non-dusting stabilizer/lubricant combinations for vinyl chloride polymers which comprise a mixture—combined in the melt—of lubricants, metal soaps of a long-chain aliphatic carboxylic acid and basic lead salts of inorganic or organic acids. However, experience has shown that it is difficult, if not impossible, to produce dibasic lead soaps (stearates) and, in particular, defined quantities of dibasic lead soaps in addition to neutral lead soaps (stearates), by the melt process. Accordingly, it is proposed in the above publications to introduce separately prepared dibasic lead soaps into the melt of lubricants and/or neutral lead soaps.

DESCRIPTION OF THE INVENTION

The present invention affords a simple process by which dibasic lead fatty acid salts can be produced in situ by the melt process. More particularly, the invention seeks to provide a melt process in which predetermined quantitative ratios of neutral lead soaps to dibasic lead soaps of the type mentioned can be established by the melt process. Through the new process, the invention seeks to provide a simple way of melt phase producing stabilizer systems for halogenated polymers, more especially polyvinyl chloride, which combines mixing of the constituents with the production of essential components in the melt.

The accomplishment of this invention is based on the surprising discovery that basic lead soaps can be produced in the melt from neutral lead soaps providing certain mixture components are present in the melt.

Accordingly, the present invention relates to a process for the production of plumbous lead-fatty acid salts by reaction of plumbous oxide with a melt of those fatty acids which form lead salts, especially in the production of stabilizer mixtures for halogenated polymers, particularly polyvinyl chloride.

It is characterized in that, to produce dibasic lead-fatty acid salts of the formula $2PbO.Pb\,(\text{fatty acid residue})\text{hd }2$, at least one organic free hydroxyl compound, particularly one that is high boiling, is added to the melt. The process according to the invention, particularly for formation of the dibasic lead salts, uses a melt of the neutral (i.e. monobasic) lead-fatty acid salt to which organic compounds containing free hydroxyl moieties have been added. Finely divided plumbous oxide is introduced into this melt before or after the hydroxyl compounds, preferably after, that is, the invention affords a method for the synthesis of dibasic lead-fatty acid salts in melt reaction comprising: melting at least one fatty acid capable of forming a lead salt; charging thereto plumbous oxide in an amount effective to form a given amount of lead-fatty-acid salt; admixing a catalyst/initiator consisting essentially of at least one organic compound having a free hydroxyl moiety, that is high-boiling, and is capable of remaining in said melt during said synthesis; said charging and admixing being in any order and repeatable. In the presence of the free hydroxyl compounds the lead oxide undergoes a rapid reaction which is clearly reflected in the disappearance of the yellow oxide color. In the absence of the free hydroxyl compounds, the lead oxide introduced remains unreacted and suspended in the melt in the form of yellow particles.

Fatty acids useful herein include all those which are capable of forming neutral (monobasic) and dibasic lead-fatty acid salts. In particular, $C_{8-24}$, especially $C_{16-18}$ fatty acids, and mixtures thereof, may be used, preferably those that are saturated, such as lauric, myristic, palmitic and/or stearic acid.

The high-boiling organic hydroxyl compounds catalyze and/or initate formation of the dibasic lead salt in the melt reaction. Particularly suitable catalysts are compounds which remain in the reaction mixture, even during the usual final drying of the reaction product under vacuum.

In one particularly important embodiment of the invention, catalyst/initiator compounds which are compatible with the product's intended application as a stabilizer for halogen-containing polymers, especially PVC, are used. Various organic compounds containing free hydroxyl moieties which may be used in this invention are available from the wide range of compounds which have already been used as stabilizers and lubricants for PVC. Among such compounds, particularly useful are at least one: partial ester of a polyhydric alcohol such as butanediol, decanediol, diethylpropanediol, ethylene glycol, ethylhexanediol, glycerol, hexanetriol, inositol, mannitol, sorbitol, pinacol, pentanediol, propylene glycol, and the like, especially at least one of glycerol, pentaerythritol, and/or trimethylol propane; hydrogenated castor oil; $C_{6-32}$, preferably $C_{8-24}$, fatty alcohol.

Suitable partial esters of polyhydric alcohols, more especially pentaerythritol and/or trimethylol propane, and their use in stabilizer-lubricant combinations for molding compositions based on polyvinyl chloride are disclosed in U.S. Pat. No. 4,421,886 and corresponding published German patent application No. 26 52 328. This U.S. patent is incorporated herein by reference, and describes partial esters of pentaerythritol and/or trimethylol propane with $C_{8-22}$-fatty acids as components for mixing with already prepared polybasic lead compounds, to be used as a polymer stabilizer. The partial esters are prepared in known manner by partial esterification of polyhydric alcohols with $C_{8-22}$-fatty acids, optionally in the presence of the usual catalysts. Suitable fatty acids include at least one of: caprylic acid, capric acid, lauric acid, myristic acid, palmitic acid, stearic acid or behenic acid. Particular significance is attributed to the stearic acid esters and, in conjunction therewith, to the corresponding lead salts of stearic acid.

The organic hydroxyl compounds should contain one or more free hydroxyl moieties. Fatty alcohols containing only one free hydroxyl moiety and also partial esters, for example of pentaerythritol, containing one, two or even three free hydroxyl moieties are suitable. The same applies to partial esters of other polyhydric alcohols, such as glycerol or trimethylol propane. The free hydroxyl moieties (or rather the corresponding organic compounds containing free hydroxyl moieties) only have to be used in very low concentrations to initiate and promote the hitherto inaccessible melt-phase reaction of plumbous oxide (litharge) with neutral lead salt to form dibasic lead salt. Catalytic quantities of the hydroxyl moieties may be minimally sufficient. It is preferred to use quantities of at least about 5% by weight of the free hydroxyl compounds based on the lead salts in the end product. However, the organic compound containing hydroxyl moieties may also be used in large quantities of any size or even in large excesses. In one preferred embodiment of the invention, the quantity in which the free hydroxyl compound is used is determined by the intended application as a stabilizer and lubricant composition. In this instance, the organic component containing the hydroxyl moieties used in this invention should be one which is wanted in the system and which may be present either in partial quantities or in the total quantity necessary during formation of the dibasic lead salts by melt-phase reaction.

The reaction of litharge with the melt of a neutral lead salt in the presence of the free hydroxyl compounds gives reaction melts of which the color depends upon the type of additive selected. The lightest colors were observed where pentaerythritol partial esters were used. Accordingly, particular significance is attributed to these mixing components for the purposes for the invention. It can be of particular advantage to use pentaerythritol diesters and, more especially, corresponding partial esters with stearic acid.

In one preferred embodiment of the inventive process, predeterminable ratio mixtures of neutral and dibasic lead-fatty acid salts are prepared by initially forming neutral lead salts from lead oxide and fatty acids by reaction in the melt. The free hydroxyl containing organic compound is added to the melt of the neutral lead salt, after which additional plumbous oxide is introduced into the melt in such quantities that, on completion of the reaction of this additional plumbous oxide, a predetermined ratio of a mixture of neutral and basic lead salts is obtained. Under certain conditions, it is possible completely to convert the neutral lead salt formed beforehand to the dibasic lead salt. To this end, the organic hydroxyl compound must be present in the melt in a quantity of at least 25% by weight and preferably in a quantity of 40% by weight, based on the end product. In this case, glycerol distearate may be used with particular advantage as the organic free hydroxyl compound. Generally, predetermined ratios by weight of dibasic lead salts to neutral lead salts of from 1:0–50 may be established in preferred embodiments of the invention. The ratios by weight are preferably in the range from 1:0.1–10, most preferably 1:0.5–3.

In another embodiment of the invention, it may be desirable to combine the melt phase of the lead salts with a melt of corresponding calcium, magnesium or aluminum, preferably calcium soaps or to prepare the calcium or other metal soaps of the corresponding fatty acids in the melt of the lead salts. Complex stabilizer mixtures may be prepared particularly easily in this way. In this case, salt formation is preferably carried out in the following reaction steps: first, the neutral (monobasic) lead salt is prepared in known manner by reacting a melt of the fatty acids with plumbous oxide. The desired proportion of corresponding calcium or other metal soap is then formed in this melt of the neutral lead salt. To this end, it is possible from the outset to use correspondingly large (i.e. excess) quantities of the fatty acid or, alternatively, to add further fatty acid. Then a soap-forming metal is added, such as magnesium oxide, hydroxide, or carbonate; or aluminum oxide or hydroxide; but preferably calcium oxide, carbonate, or hydroxide. In the concluding reaction step, the predetermined quantity of dibasic lead salt is formed by the introduction of more plumbous oxide. The organic hydroxyl compound used in accordance with the invention may be added to the melt at the outset or at any time before the concluding reaction step for forming the dibasic lead salt. However, it can be of particular advantage first to carry out or conclude formation of the neutral lead salt, second formation of the calcium soap in the absence of the organic free hydroxyl compound and third to add the organic free hydroxyl compound to the reaction mixture, thus forming the dibasic lead soaps.

If desired, the melt-phase reaction according to the invention may be carried out in the presence of other inert components dissolved and/or suspended in the melt, of the type commonly used in particular in stabilizer and/or lubricant systems for halogen-containing polymers, especially PVC. More particularly, it is also possible in accordance with the invention to add the components additionally required for the intended application to the melt systems accumulating as reaction product. In this way, it is possible in accordance with the teachings of the prior art to obtain non-dusting stabilizer-lubricant combinations which may be granulated or converted into any other finely divided form.

In terms of practical application, the basic and neutral salts obtained by the melt process behave similarly to precipitated soaps. In addition, the melt salts have the advantage that they can be produced without polluting the environment in any way and enable stabilizer systems for rigid PVC or other halogen-containing polymers to be produced from a lead compound, namely lead oxide, in virtually a single process step. The granular soap mixtures produced by the process according to the invention may be processed with PVC in the usual way to form dry blends. Using fluid mixers, they may readily be dispersed in the resin at the usual mixing temperatures and may be processed in extruders, for example to form PVC pipes. The residual stability, as measured on the extruded moldings, is sufficient to guarantee even the reprocessing of "startup" material.

EXAMPLES

EXAMPLE 1

In an open glass vessel equipped with a stirrer and thermometer, 56.6 g (0.21 mol) of a technical $C_{16-18}$ fatty acid (MW 270) and 45 g of hard paraffin (Mp.100° C.) were melted and heated to 150° C. 23.4 g (0.105 mol) of litharge were then introduced into the melt over a period of 2 minutes with stirring, the reaction temperature being kept at 150°–160° C. After stirring for another 2 minutes, a clear yellowish melt had formed 9 g of pentaerythritol distearate were then stirred into the melt, another 18 g (0.08 mol) of litharge were added over a period of 4 minutes and the melt was stirred for 30 minutes at 150° C. By that time, the lead oxide added had dissolved. The reaction mixture was in the form of a sediment-free, clouded yellowish melt which solidified on cooling (Mp. 103° C.).

EXAMPLE 2

As in Example 1, 56.6 g (0.21 mol) of technical $C_{16-18}$ fatty acid (MW 270) and 45 g of hard paraffin (Mp. 100° C.) were heated to 150° C. and 23.4 g (0.105 ml) of litharge added. After the lead oxide had dissolved, 9 g of technical glycerol distearate and another 18 g (0.08 mol) of litharge were introduced. The melt was then stirred some more at 150° C., the litharge added dissolving in 40 minutes. Thereafter, the reaction mixture was in the form of a sediment-free, almost clear, reddish melt which solidified on cooling (Mp. 100° C.).

EXAMPLE 3

As in Example 1, 56.6 g (0.21 mol) of technical $C_{16-18}$ fatty acid (MW 270) and 45 g of hard paraffin (Mp. 100° C.) were heated to 150° C. and 24.4 g (0.105 mol) of litharge added. After the lead oxide had dissolved, 9 g of behenyl alcohol and another 18 g ( 0.08 mol) of litharge were introduced into the melt. The melt was stirred some more at 150° C. until, after 60 minutes, the lead oxide added had completely dissolved. The reaction mixture was in the form of an almost clear, yellowish melt which solidified on cooling (Mp. 93° C.).

EXAMPLE 4

As in Example 1, 92.8 g (0.34 mol) of technical $C_{16-18}$ fatty acid (MW 270 and 27 g of hard paraffin (Mp. 100° C.) were heated to 150° C. and 38.3 g (0.17 mol) of litharge added. After the lead oxide had dissolved, 10.0 g of pentaerythritol, 5 g of bisphenol A and another 30.0 g (0.13 mol) of litharge were successively added. The melt was stirred for 20 minutes at 150°–155° C. By that time, the lead oxide added had dissolved. The reaction mixture was in the form of a sediment-free whitish melt with brown tinges which solidified on cooling to a yellowish solid.

EXAMPLE 5

As in Example 1, 92.8 g (0.34 mol) of technical $C_{16-18}$ fatty acid (MW 270) and 27 g of hard paraffin (Mp. 100° C.) were heated to 150° C. and 38.3 g (0.17 mol) of litharge added. After the lead oxide had dissolved, 10 g of trimethylol propane, 5 g of bisphenol A and another 30.0 g (0.13 mol) of litharge were successively introduced into the melt. The melt was then stirred for 30 minutes at 150° to 155° C. Thereafter, the reaction mixture was in the form of a clouded, sediment-free melt. The mixture solidified on cooling to a yellow-tinged solid.

EXAMPLE 6

As in Example 1, 92.8 g (0.34 mol) of technical $C_{6-18}$ fatty acid (MW 270) and 27 g of hard paraffin (Mp. 100° C.) were heated to 150° C. and 38.3 g (0.017 mole) of litharge added. After the neutral lead salt had formed, 10 g of hydrogenated castor oil, 5 g of bisphenol A and 30.0 g (0.13 mol) of litharge were successively added. The melt was then stirred for another 40 minutes at 150°–160° C., by which time the lead oxide added had dissolved. The reaction mixture was present in the form of a sediment-free, clouded gray melt which solidified on cooling to a gray-tinged solid.

EXAMPLE 7

In an open glass vessel equipped with a stirrer and thermometer, 69.1 g (0.26 mol) of technical $C_{16-18}$ fatty acid (MW 270) and 38.3 g of hard paraffin (Mp. 100° C.) were heated to 150° C., after which 20 g (0.09 mol) of litharge and 2.9 g (0.04 mol) of calcium hydroxide were added with stirring. After the lead oxide and calcium hydroxide had dissolved, 7.6 g of pentaerythritol distearate and then 15.1 g (0.068 mol) of litharge were introduced into the melt. The melt was then stirred some more at 150° C. until, after 30 minutes, the lead oxide added had dissolved. The reaction mixture was in the form of a sediment-free, clouded yellowish melt which solidified on cooling (Mp 101° C.).

EXAMPLE 8

As in Example 7, 60.7 g (0.23 mol) of technical $C_{16-18}$ fatty acid (MW 270) and 42.8 g of hard paraffin (Mp 100° C.) were heated to 150° C., after which 22.3 g (0.10 mol) of litharge and 1 g (0.014 mol) of calcium hydroxide were successively introduced into the melt with stirring. After the lead oxide and calcium hydroxide had dissolved, 8.5 g of pentaerythritol distearate and then 17.0 g (0.076 mol) of litharge were added and the melt stirred until, after 40 minutes, there was no sediment. The clouded, yellowish reaction mixture solidified on cooling (Mp 101° C.).

EXAMPLE 9

In an open glass vessel equipped with a stirrer and thermometer, 158 g (0.59 mol) of technical $C_{16-18}$ fatty acid (MW 270) were heated to 150° C. 65.6 g (0.29 mol)

of litharge were then introduced into the melt with stirring. After the lead oxide had dissolved, 350 g of pentaerythritol distearate were added. The melt was reheated to 150° C. and 131.1 g (0.59 mol) of litharge added. The melt was then stirred at 150°–160° C. until, after 10 minutes, there was no sediment. The clouded, yellow-tinged melt solidified on cooling (Mp. 97° C.).

EXAMPLE 10

As in Example 9, 211.4 g (0.78 mol) of technical $C_{16\text{-}18}$ fatty acid (MW 270) were heated to 150° C. 87.4 g (0.39 mol) of litharge were then dissolved in the melt. Thereafter, 233.5 g of technical glycerol distearate and, after the temperature of the melt had risen back to 150°–160° C., 174.8 g (0.78 mol) of litharge were introduced. The melt was stirred at 150°–160° C. until, after 30 minutes, it was free from sediment. The clear, brownish melt solidified on cooling (Mp. 97° C.).

EXAMPLE 11

As in Example 9, 211.4 g (0.78 mol) of technical $C_{16\text{-}18}$ fatty acid (MW 270) were heated to 150° C. 87.4 g (0.39 mol) of litharge were dissolved in the melt, after which 233.5 g of technical glycerol monostearate were added. The melt was then reheated to 150°–160° C., after which 174.8 g (0.78 mol) of litharge were introduced. Thereafter, the melt was stirred for 30 minutes at 150°–160° C. until it was free from sediment. The clear, brownish reaction mixture solidified on cooling (Mp. 93° C.).

We claim:

1. A method for the synthesis of dibasic lead-fatty acid salts in a melt reaction comprising:
   melting at least one fatty acid capable of forming a monobasic or dibasic lead-fatty acid salt;
   charging thereto plumbous oxide in an amount effective to form a given amount of said dibasic lead-fatty acid salt;
   admixing a catalyst/initiator consisting essentially of at least one organic compound having a free hydroxyl moiety, that is high-boiling, and is capable of remaining in said melt during said synthesis; said charging and admixing being in any order and repeatable.

2. The method of claim 1 wherein said at least one fatty acid has 12 to 24 carbon atoms.

3. The method of claim 1 wherein said at least one fatty acid has 16 to 18 carbon atoms.

4. The method of claim 1 wherein said catalyst/initiator consists essentially of at least one: $C_{8\text{-}22}$-fatty acid partial ester of a polyhydric alcohol; hydrogenated vegetable oil; or $C_{6\text{-}32}$-fatty alcohol.

5. The method of claim 1 wherein said catalyst/initiator consists essentially of at least one: $C_{8\text{-}22}$-fatty acid partial ester of glycerol or pentaerythritol; hydrogenated castor oil; or $C_{8\text{-}24}$-fatty alcohol.

6. The method of claim 1 wherein said catalyst/initiator consists essentially of a stearic acid ester of pentaerythritol, glycerol, trimethylol propane, or a mixture thereof.

7. The method of claim 1 wherein said catalyst/initiator consists essentially of pentaerythritol stearate or distearate, glycerol stearate or distearate, behenyl alcohol, pentaerythritol, bisphenol A, trimethylol propane, hydrogenated castor oil, or a mixture thereof.

8. The method of claim 1 wherein said catalyst/initiator consists essentially of pentaerythritol mono- or distearate, or their mixture.

9. The method of claim 3 wherein said catalyst/initiator consists essentially of pentaerythritol stearate or distearate, glycerol stearate or distearate, behenyl alcohol, pentaerythritol, bisphenol A, trimethylol propane, hydrogenated castor oil, or a mixture thereof.

10. The method of claim 3 wherein said catalyst/initiator consists essentially of pentaerythritol mono- or distearate, or their mixture.

11. The method of claim 1 wherein said catalyst/initiator is employed in an amount of at least 5% by weight, based upon the total weight of lead salt in the synthesis end product.

12. The method of claim 9 wherein said catalyst/initiator is employed in an amount of at least 5% by weight, based upon the total weight of lead salt in the synthesis end product.

13. The method of claim 1 wherein said admixing is effected prior to said charging.

14. The method of claim 1 wherein a mixture of neutral lead-fatty acid salt and dibasic lead-fatty acid salt in a predetermined ratio is obtained by sequentially:
   forming substantially neutral lead-fatty acid salt by charging said plumbous oxide;
   admixing said catalyst/initiator; and
   charging additional plumbous oxide to convert said neutral lead-fatty acid salt to dibasic lead-fatty acid salt, in an amount determined by the additional amount of said plumbous oxide.

15. The method of claim 7 wherein a mixture of neutral lead-fatty acid salt and dibasic lead-fatty acid salt in a predetermined ratio is obtained by sequentially:
   forming substantially neutral lead-fatty acid salt by charging said plumbous oxide;
   admixing said catalyst/initiator; and
   charging additional plumbous oxide to convert said neutral lead-fatty acid salt to dibasic lead-fatty acid salt, in an amount determined by the additional amount of said plumbous oxide.

16. The method of claim 10 wherein a mixture of neutral lead-fatty acid salt and dibasic lead-fatty acid salt in a predetermined ratio is obtained by sequentially:
   forming substantially neutral lead-fatty acid salt by charging said plumbous oxide;
   admixing said catalyst/initiator; and
   charging additional plumbous oxide to convert said neutral lead-fatty acid salt to dibasic lead-fatty acid salt, in an amount determined by the additional amount of said plumbous oxide.

17. The method of claim 14 wherein said predetermined ratio of dibasic to neutral lead-fatty acid salts is 1:0.1–10.

18. The method of claim 16 wherein said predetermined ratio of dibasic to neutral lead-fatty acid salts is 1:0.5–3.

19. The method of claim 1 wherein (1) sufficient of said plumbous oxide is charged to said melt to form neutral lead-fatty acid salt, (2) at least one calcium, magnesium, or aluminum soap of said fatty acid is introduced to the reaction melt, and then (3) said catalyst/initiator is admixed, together with sufficient additional plumbous oxide, to form a desired proportion of dibasic lead-fatty acid.

20. The method of claim 19 wherein said soap is calcium stearate.

21. The method of claim 19 wherein said calcium, magnesium, or aluminum salts are introduced by in situ formation in said melt, by adding; calcium oxide, hydroxide or carbonate; magnesium oxide, hydroxide, or carbonate; aluminum oxide or hydroxide; or any mixture thereof; to the fatty acids of said melt.

22. The method of claim 21 wherein calcium oxide, hydroxide, or their mixture is added.

23. The method of claim 1 wherein inert components of stabilizer and lubricant systems for halogen-containing polymers are added to the reaction melt.

* * * * *

UNITED STATES PATENT AND TRADEMARK OFFICE
CERTIFICATE OF CORRECTION

PATENT NO. : 4,744,927
DATED : May 17, 1988
INVENTOR(S) : Worschech et al

It is certified that error appears in the above-identified patent and that said Letters Patent is hereby corrected as shown below:

On the cover page, the "Assignee" should read --Neynaber Chemie GmbH, Loxstedt, Fed. Rep. of Germany--.

Signed and Sealed this

Twenty-second Day of August, 1989

Attest:

DONALD J. QUIGG

*Attesting Officer*    *Commissioner of Patents and Trademarks*